(12) United States Patent
Wang et al.

(10) Patent No.: US 7,286,235 B2
(45) Date of Patent: Oct. 23, 2007

(54) LONG-RANGE SURFACE PLASMON RESONANCE DEVICE UTILIZING NANO-SCALE POROUS DIELECTRIC AND METHOD OF FABRICATING THE SAME

(75) Inventors: Fu Wang, Gyeonggi-do (KR); Jang-seok Ma, Gyeonggi-do (KR); Gyeong-sik Ok, Busan (KR)

(73) Assignee: Samsung Electronics Co., Ltd. (KR)

( * ) Notice: Subject to any disclaimer, the term of this patent is extended or adjusted under 35 U.S.C. 154(b) by 82 days.

(21) Appl. No.: 11/205,995

(22) Filed: Aug. 17, 2005

(65) Prior Publication Data

US 2006/0170927 A1    Aug. 3, 2006

(30) Foreign Application Priority Data

Jan. 29, 2005   (KR) .................... 10-2005-0008345

(51) Int. Cl.
*G01N 21/55*   (2006.01)
(52) U.S. Cl. .................... 356/445; 433/82.05
(58) Field of Classification Search ............ 356/445; 422/82.05
See application file for complete search history.

(56) References Cited

U.S. PATENT DOCUMENTS 5,327,225 A * 7/1994 Bender et al. ............ 356/445
6,787,601 B2 * 9/2004 Lamola et al. ............ 524/714

FOREIGN PATENT DOCUMENTS

KR    10-2004-0102847    12/2004

OTHER PUBLICATIONS

Korean Intellectual Property Office Action Translation; Application No. 10-2005-0008345 (Jun. 7, 2006).

* cited by examiner

Primary Examiner—Richard A. Rosenberger
(74) Attorney, Agent, or Firm—Cantor Colburn LLP

(57) ABSTRACT

A surface plasmon resonance device includes a transparent substrate, a porous dielectric layer formed on a top surface of the transparent substrate, a thin metal layer formed on the porous dielectric layer, and a prism attached on a bottom surface of the transparent layer.

21 Claims, 7 Drawing Sheets

FIG. 9

```
┌─────────────────────────────────────┐
│   DETERMINE OPTIMIZED PARAMETERS OF │
│   SURFACE PLASMON RESONANCE         │
│   DEVICE BY SIMULATION              │
└─────────────────────────────────────┘
                  │
┌─────────────────────────────────────┐
│   DISPERSE POROGEN IN DIELECTRIC    │
│   MATERIAL ACCORDING TO DETERMINED  │
│   OPTIMIZED PARAMETERS              │
└─────────────────────────────────────┘
                  │
┌─────────────────────────────────────┐
│   DEPOSIT DIELECTRIC MATERIAL ON    │
│   TRANSPARENT SUBSTRATE TO          │
│   A PREDETERMINED THICKNESS         │
└─────────────────────────────────────┘
                  │
┌─────────────────────────────────────┐
│   PERFORM HEAT TREATMENT TO FORM    │
│   POROUS DIELECTRIC LAYER ON        │
│   TRANSPARENT SUBSTRATE             │
└─────────────────────────────────────┘
                  │
┌─────────────────────────────────────┐
│   DEPOSIT THIN METAL LAYER ON POROUS│
│   DIELECTRIC LAYER TO               │
│   A PREDETERMINED THICKNESS         │
└─────────────────────────────────────┘
```

LONG-RANGE SURFACE PLASMON RESONANCE DEVICE UTILIZING NANO-SCALE POROUS DIELECTRIC AND METHOD OF FABRICATING THE SAME

CROSS-REFERENCE TO RELATED PATENT APPLICATION

This application claims the benefit of Korean Patent Application No. 10-2005-0008345, filed on Jan. 29, 2005, in the Korean Intellectual Property Office, the disclosure of which is incorporated herein in its entirety by reference.

BACKGROUND OF THE INVENTION

1. Field of the Invention

The present invention relates to a long-range surface plasmon resonance device utilizing a nano-scale porous dielectric and a method of fabricating the same, and more particularly, to a long-range surface plasmon resonance device having high resolution and high sensitivity by properly adjusting a refractive index of a porous dielectric and a size and density of porosities formed in a porous dielectric layer and to a method of fabricating such a long-range surface plasmon resonance device.

2. Description of the Related Art

Fluorescence analysis has been widely used as a bio-sample analysis method. According to the fluorescence analysis, each of the biomolecules is first colored by a fluorescent dye having a typical reaction wavelength and information such as an ingredient of the biosample is then analyzed from a spectrum of light emitted from the sample by irradiating light to the biosample mixed with a variety of biomolecules. However, the fluorescence analysis has problems in that the coloring process for the biosample is complicated and the fluorescent dye is very expensive. To solve these problems, a variety of methods for analyzing the biomolecules without using the fluorescent dye have been developed. One of them is a method using surface plasmon resonance. The plasmon is a kind of surface electromagnetic waves traveling along interface surfaces between a thin metal layer and a dielectric and a surface plasmon resonance phenomenon is produced by a charge density oscillation generated on a surface of the thin metal layer.

FIG. 1 shows a conventional structure incurring such surface plasmon resonance.

Referring to FIG. 1, a prism 10 and a thin metal layer 12 are respectively attached on bottom and top surfaces of a transparent substrate 11 and a fluid sample 13 to be measured is disposed on the thin metal layer 12. Here, the transparent substrate 11 and the prism 10 are formed of materials having the same refractive index. As shown in FIG. 1, when light is directed to the boundary surface between the thin metal layer 12 and the transparent substrate 11 at an angle greater than a total reflection angle, a total reflection is generated. Thus, an evanescent wave having a very short effective length is generated and advances from the reflective surface to the thin metal layer 12. Since a thickness of the thin metal layer 12 is less than the effective length of the evanescent wave, the evanescent wave can reach the liquid sample disposed on the thin metal layer 12. At this point, when the wavelength of the incident light is continuously varied, the light is absorbed at a specific wavelength and a charge density oscillation appears on the surface of the thin metal layer 12. This is called an excitation of the surface plasmon. This phenomenon may be generated at a specific incident angle when the light incident angle is continuously varied instead of varying the wavelength. The wavelength or incident angle when the surface plasmon is excited is determined by the refraction index of the liquid sample 13.

FIG. 3 shows a graph illustrating variation of the reflectivity according to the variation of the wavelength. A reflectivity curve indicated by the reference character A is a case where the liquid sample 13 is water. This shows that the surface plasmon resonance is generated at a wavelength of about 700 nm and the reflectivity is steeply reduced. When the refractive index varies by dissolving a biomaterial in the water, the resonance wavelength varies as indicated by a reflectivity A'. When this principle is used, it becomes possible to detect a specific biomolecule from the liquid sample.

However, when this method is used, since the curve variation of the reflectivity is very small and a width of the curve is wide, the resolution and sensitivity are not enough high. In addition, since the effective distance of the evanescent wave is very short, it is difficult to measure a relative large sample.

FIG. 2 shows a structure for solving the above-described problem. In this structure, a buffer layer 14 formed of dielectric is disposed between a transparent substrate 11 and a thin metal layer 12. In this case, since the effective length of the evanescent wave is increased, it becomes possible to measure a relative large sample. This is called a long-range surface plasmon resonance. In addition, as can be noted from reflective curves B and B' of FIG. 3, since a very sharp reflective curve is formed, higher resolution and sensitivity can be obtained. In FIG. 3, the reflectivity curve B is for a case where the liquid sample 13 is pure water and the reflectivity curve B' is for a case where there is refractive index is varied by adding other material to the water. When comparing the reflectivity curves B and B' with the reflectivity curves A and A', it can be noted that the curves B and B' are very sharp.

However, there are very few dielectric materials that can be used for the buffer layer 14. That is, the buffer layer 14 should be made of a transparent material that can be coated on the transparent substrate 11 while having a refractive index similar to that of the liquid sample so that the surface plasmon resonance can be generated. There are only two materials, Teflon and $MgF_2$ that can satisfy the above conditions. However, since these materials have fixed refractive indexes, an optimal reflectivity curve cannot be provided according to the liquid sample. That is, even when the reflective curve becomes sharp, noise increases by outer conditions, thereby making it difficult to actually improve the resolution.

SUMMARY OF THE INVENTION

The present invention provides a surface plasmon resonance device including a buffer layer having a properly adjusted refractive index. That is, the present invention provides a long-range surface plasmon resonance device that can provide optimum detection conditions by properly adjusting a refractive index of the buffer layer using a nano-scale porous dielectric and a method of fabricating such a long-range surface plasmon resonance device.

According to an aspect of the present invention, there is provided a surface plasmon resonance device comprising: a transparent substrate; a porous dielectric layer formed on a top surface of the transparent substrate; a thin metal layer formed on the porous dielectric layer; and a prism attached on a bottom surface of the transparent layer.

The porous dielectric layer may have an adjusted refractive index obtained by adjusting a density of porosities formed in the porous dielectric layer. The porous dielectric layer may be formed by vaporizing porogen through a heat treatment after the porogen is dispersed in a dielectric material. The dielectric material may contain at least one of silane and siloxane polymer and the porogen may contain cyclodextrin. A size of each porosity formed in the porous dielectric layer may be less than 10 nm.

The thin metal layer may contain Au and a thickness of the thin metal layer may be less than 20 nm.

The prism may have a refractive index identical to that of the transparent substrate.

According to another aspect of the present invention, there is provided a method for fabricating a surface plasmon resonance device, the method including: mixing and dispersing porogen with and in a dielectric material; depositing the dielectric material mixed with the porogen on a transparent substrate to a predetermined thickness; performing a heat treatment to form a porous dielectric layer by crystallizing the dielectric material and vaporizing the porogen dispersed in the dielectric material; depositing a thin metal layer on the porous dielectric layer; and attaching a prism on a bottom surface of the transparent substrate.

A mixture ratio of the dielectric material and the porogen may be determined according to parameters of the surface plasmon resonance device that is optimized according to a sample that is to be measured. The parameters may include a refractive index of the porous dielectric layer, a thickness of the porous dielectric layer, a refractive index of the transparent substrate, a thickness of the thin metal layer, and a wavelength of a light source. A mixture ratio of the dielectric material and the porogen may be determined according to a refractive index of the porous dielectric layer.

The heat treatment may be performed at 450° C.

BRIEF DESCRIPTION OF THE DRAWINGS

The above and other features and advantages of the present invention will become more apparent by describing in detail exemplary embodiments thereof with reference to the attached drawings in which:

FIG. 9 is a flowchart illustrating a method of fabricating a surface plasmon resonance device according to an embodiment of the present invention.

DETAILED DESCRIPTION OF THE INVENTION

The present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art.

As described above, a dielectric generating a surface plasmon resonance while having an optimum refractive index with respect to a specific liquid sample has not been found. Therefore, there is a need to properly process a dielectric material generating the surface plasmon resonance so that the dielectric material can have a desired refractive index. Porous dielectric is well known as a material that can realize the need. In order to make the porous dielectric, after porogen formed of organic particles is dispersed in a dielectric, the porogen is vaporized through a heat treatment. As the porogen is vaporized, spaces where the porogen exists are hollowed so that a plurality of micro-porosities are formed in the dielectric. At this point, according to the ratio of the porogen to the dielectric, a refractive index of the resultant porous dielectric is varied.

FIGS. 4A through 4D show a method of fabricating a long-range surface plasmon resonance device using the above-described principle.

Figure 1:
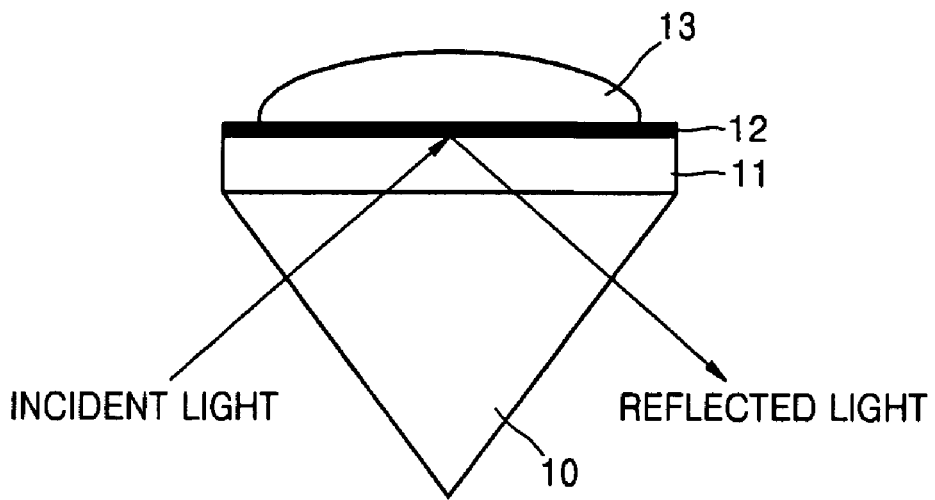
FIG. 1 is a schematic view of a prism structure generating a surface plasmon resonance.
Figure 2:
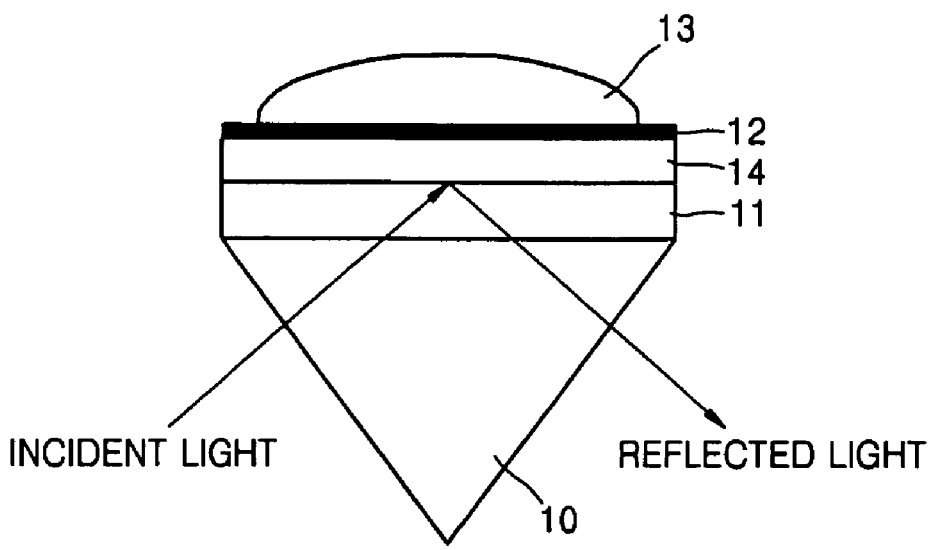
FIG. 2 is a schematic view of a prism structure generating a long-range surface plasmon resonance using a dielectric.
Figure 3:
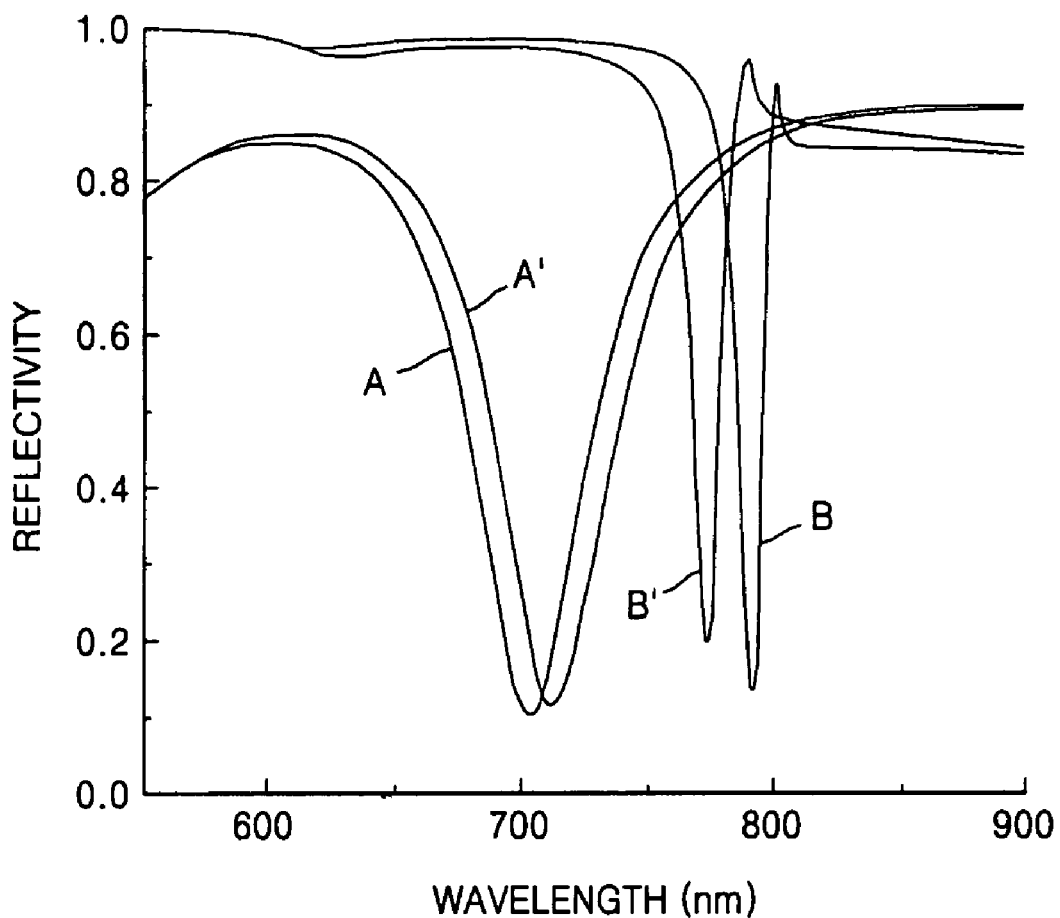
FIG. 3 is a graph illustrating light absorption by a surface plasmon resonance.
Figure 4A:
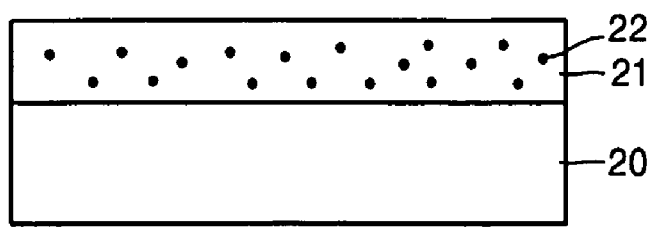
FIGS. 4A through 4D are views illustrating a method of fabricating a surface plasmon resonance device according to an embodiment of the present invention.

Referring first to FIG. 4A, a dielectric layer 21 in which porogen 22 is dispersed is formed on a transparent substrate 20 such as glass. When it is intended to detect a sample dissolved in, for example, water, since a refractive index of a buffer layer satisfying an optimal detection condition is in a range of 1-1.4, it is preferable that dielectric have a dielectric constant less than 3. As such dielectric, silane or siloxane polymer may be used. That is, silane-gel or siloxane polymer in which the porogen 22 is dispersed is deposited on the transparent substrate 20, thereby obtaining a structure as shown in FIG. 4A.

Figure 4B:
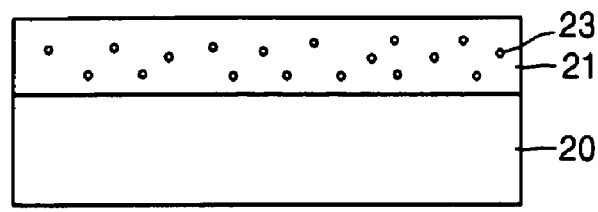

When the dielectric layer 21 formed of the silane-gel or siloxane polymer is heat-processed at a temperature of 450° C., the dielectric layer 21 starts crystallizing. In this process, the porogen 22 dispersed in the dielectric layer 21 is vaporized to evacuate the dielectric layer 21, thereby forming a plurality of porosities 23 in the dielectric layer 21 as depicted in FIG. 4B. The porous dielectric layer 21 functions as a buffer layer generating a long-range surface plasmon resonance.

Figure 4C:
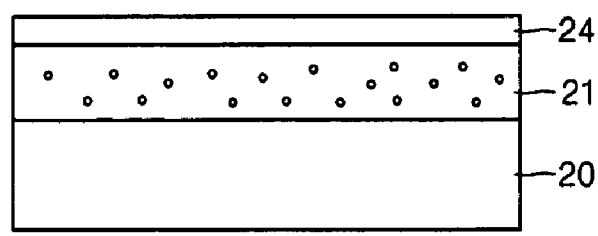
Figure 4D:
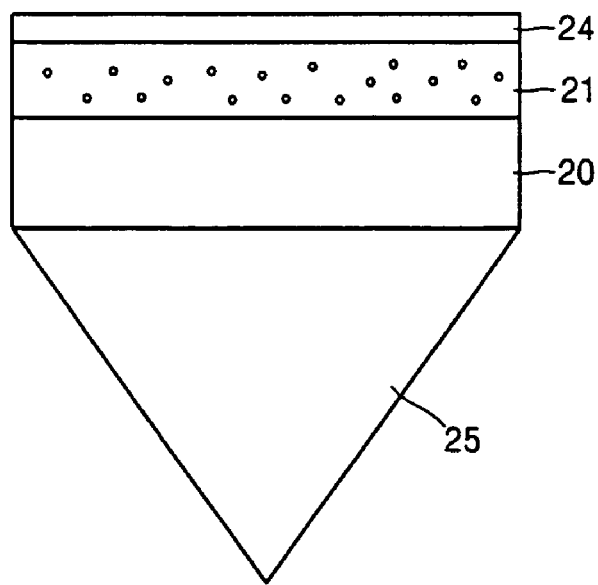

Next, as shown in FIGS. 4C and 4C, a thin metal layer 24 is deposited on the porous dielectric layer 21 and a prism 25 is attached on a bottom of the transparent substrate 20. The thin metal layer 24 may be formed of Au. A thickness of the thin metal layer 24 should be less than an effective distance of the evanescent wave generated on a boundary surface between the substrate 20 and the porous dielectric layer 21. A preferable thickness of the thin metal layer 24 is less than 20 nm. As described above, it is preferable that a refractive index of the prism be identical to that of the transparent substrate 20. Therefore, the prism 25 may be formed of a material identical to that of the transparent substrate 20. In addition, a binder such as index matching fluid and transparent elastomer attaching the prism 25 to the transparent substrate 20 is formed of a material having a refractive index identical to those of the prism 25 and the transparent substrate 20.

At this point, since the thin metal layer 24 is designed to have a thickness less than 20 nm, the porous dielectric layer 21 on which the metal layer 24 will be deposited should have a very even surface. However, since a surface of the porous dielectric layer 21 is provided with a plurality of grooves due to the porosities formed in the porous dielectric layer 21, the metal layer 24 may not be effectively deposited on the porous dielectric layer 21. When a size of each groove formed on the surface of the porous dielectric layer 21 is too large, it is difficult to uniformly apply the thin metal layer 24 on the porous dielectric layer 21. In this case, a surface plasmon resonance condition may vary and the surface plasmon resonance may not appear according to a light incident location. In order to prevent this problem, a diameter of each porosity formed in and on the dielectric layer 21 should be greatly less than a thickness of the thin metal layer 24. That is, the porous dielectric layer 21 should be designed to have porosities of a nano-scale diameter. Therefore, the porogen should be formed of an organic material having particles having a very small diameter and capable of being uniformly dispersed in the dielectric. As the porogen satisfying such conditions, cyclodextrin (CD) may be used. In this case, a diameter of each porosity formed in the dielectric layer may be less than 2 nm.

As described above, the refractive index of the porous dielectric layer 21 may be varied according to a proportion of the porogen. That is, the refractive index of the porous dielectric layer 21 is varied according to a density of the porosities formed in the porous dielectric layer 21. Therefore, after determining in advance an optimum refractive index of the porous dielectric layer, which is proper to the liquid sample that is to be detected, the proportion of the porogen is adjusted such that the porous dielectric layer 21 can have the optimum refractive index. Table 1 shows a variation of the refractive index according to a ratio of the dielectric material to the porogen in the case where cyclic silsesquioxane (CSSQ) is used as the dielectric material and the CD is used as the porogen. As can be noted from Table 1, the proportion of the porogen is increased (a density of the porosities formed in the dielectric layer is increased), and the refractive index is reduced. Referring to Table 1, a refractive index of pure CSSQ is 1.433. However, a refractive index of porous CSSQ formed using 50 wt % CD is reduced to 1.315.

TABLE 1

| SAMPLE | REFRACTIVE INDEX | DENSITY (g/cm$^2$) | POROSITY (%) |
| --- | --- | --- | --- |
| CSSQ | 1.433 | 1.447 | — |
| CSSQ/tCD 10 wt % | 1.398 | 1.311 | 9.4 |
| CSSQ/tCD 20 wt % | 1.367 | 1.216 | 16.0 |
| CSSQ/tCD 30 wt % | 1.353 | 1.114 | 23.0 |
| CSSQ/tCD 40 wt % | 1.335 | 1.073 | 25.9 |
| CSSQ/tCD 50 wt % | 1.315 | 1.017 | 29.7 |

Figure 5:
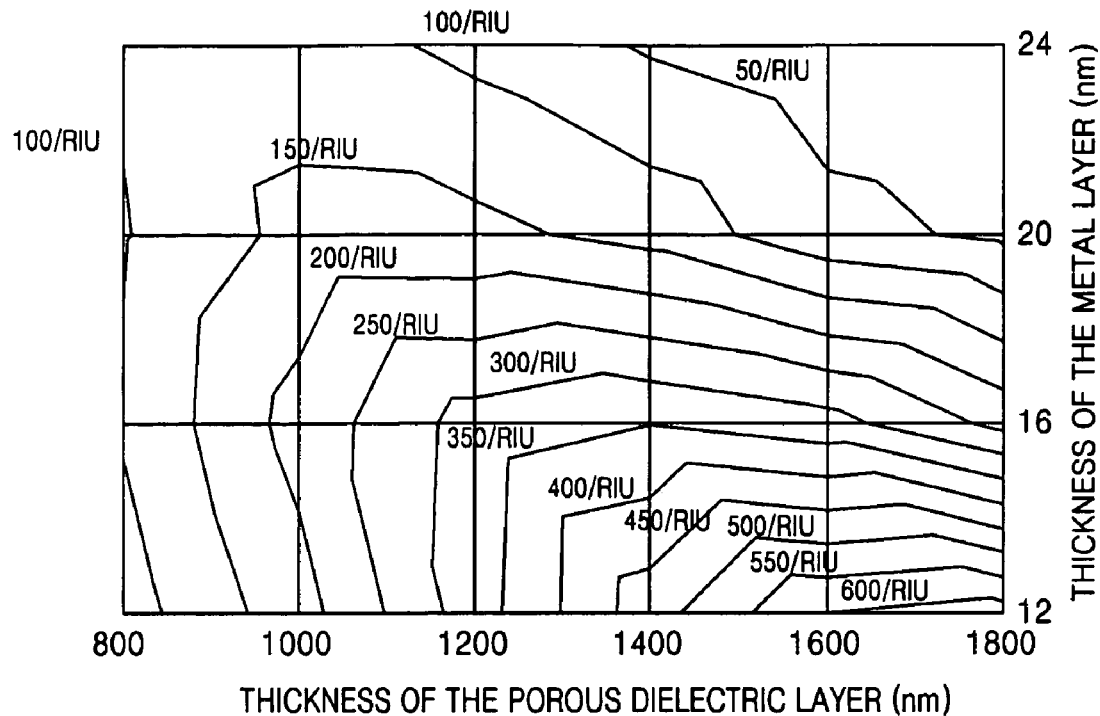
FIG. 5 is a simulation graph illustrating a reflectivity-sensitivity when thicknesses of a porous dielectric layer and a thin metal layer are varied in a state where a refractive index of the porous dielectric layer is fixed.
Figure 6:
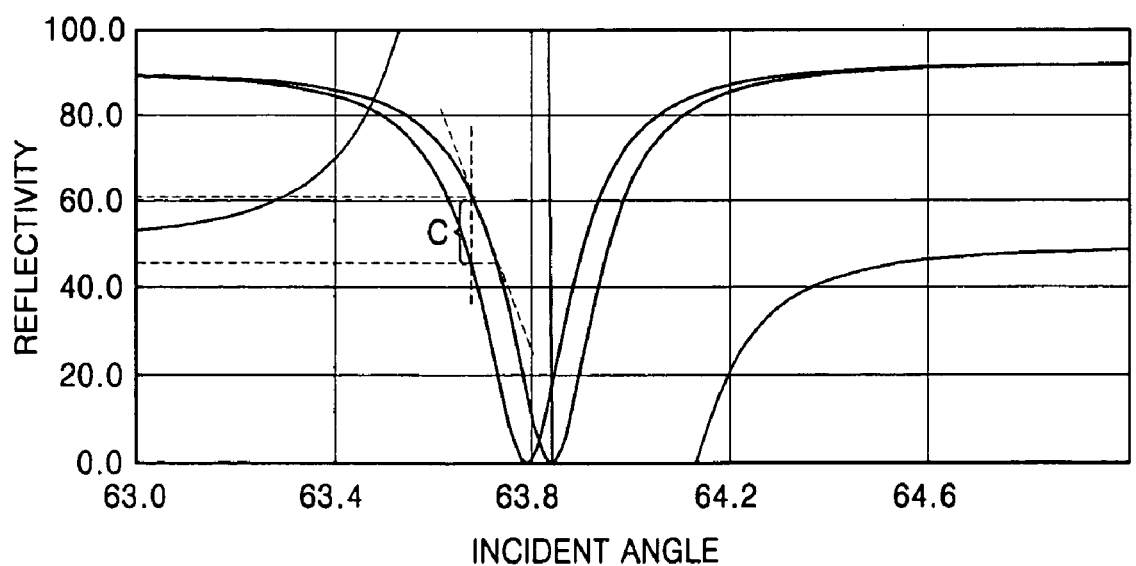
FIG. 6 is a graph illustrating a definition of a reflectivity-sensitivity.

It is possible to obtain in advance the optimum refractive index of the porous dielectric layer 21 according to the samples through a simulation. FIG. 5 shows a simulation graph illustrating a reflectivity-sensitivity when thicknesses of the porous dielectric layer 21 and the thin metal layer 24 are varied in a state where a refractive index of the porous dielectric layer 21 is fixed The reflectivity-sensitivity represents a variation of an intensity of light at half-width when the reflectivity curve is shifted due to the refractive index variation of the liquid sample. In FIG. 6, when the light incident angle at the boundary surface between the transparent substrate 20 and the porous dielectric layer through the prism 25 is varied from 63° to 65°, an initial reflectivity of the liquid sample is exampled in a left side of the curve. When a specific biomolecule is contained in the liquid sample, the refractive index of the sample is varied to move the reflectivity curve rightward. Accordingly, the intensity of the reflected light at an incident angle corresponding to the half-width of the initial reflectivity curve is increased by C. At this point, the higher the increase of the intensity of the reflected light, the higher the resolution and sensitivity. Therefore, the reflectivity-sensitivity can be defined as a variation amount of the reflectivity at the half-width per a variation amount of the refractive index. As a unit of the reflectivity-sensitivity, "/RIU(refractive index unit)" is used.

FIG. 5 shows a simulation result when water (having a reflective index n of 1.333) is used as the liquid test solution, Au is used as a thin metal layer 24, a refractive index n of the porous dielectric layer 21 is 1.333, an inner angle of the prism is 60°, and a refractive index n of the prism at a 632.8 nm wavelength is 1.51509. As shown in FIG. 5, the lower the thickness of the thin metal layer 24 and the higher the thickness of the porous dielectric layer 21, the greater the increase of the reflectivity-sensitivity.

Figure 7A:
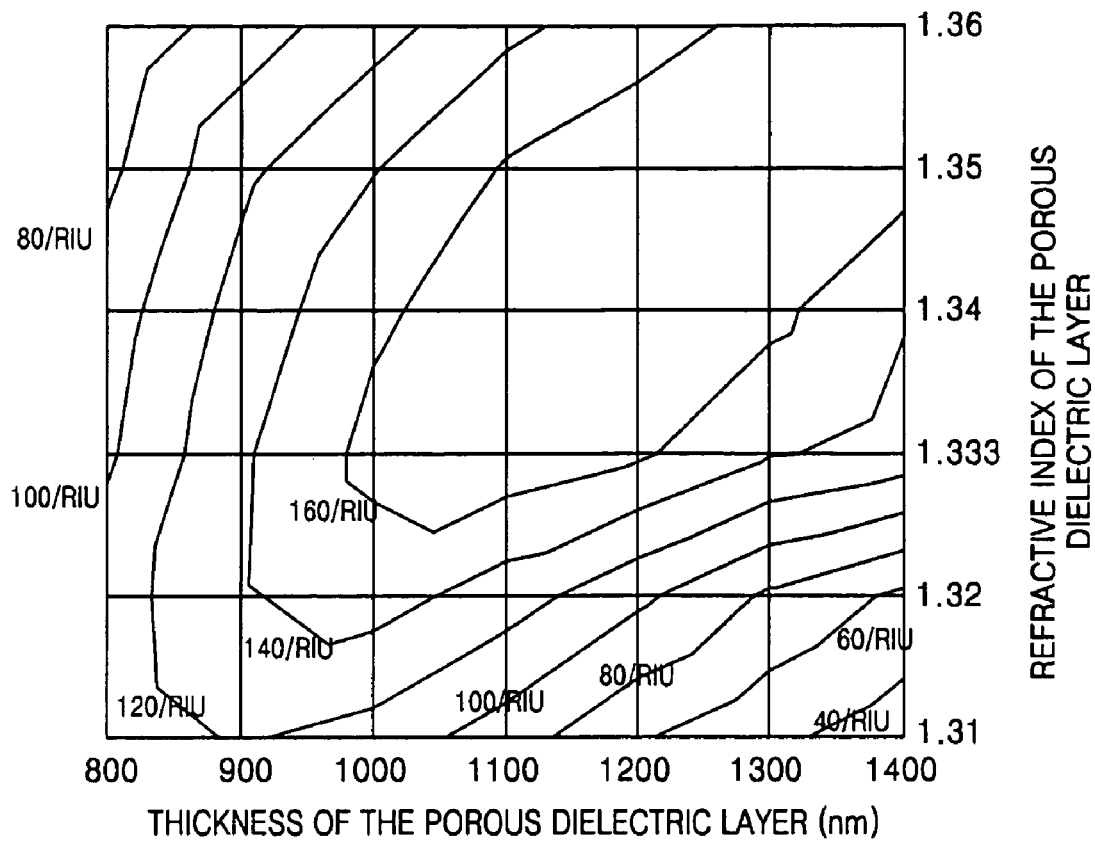
FIGS. 7A through 8B are graphs illustrating a thickness of a porous dielectric layer and a refractive index in a state where a thickness of a thin metal layer is fixed.
Figure 7B:
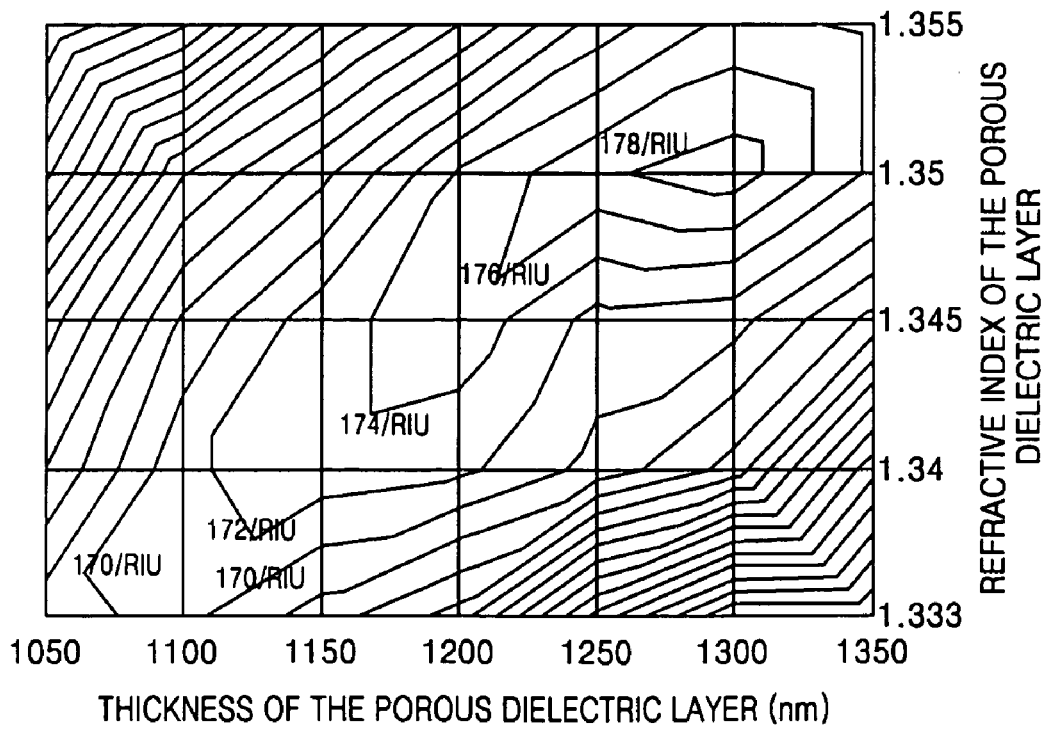

FIGS. 7A and 7B show a simulation result of the variation of the reflectivity-sensitivity according to the variations of a thickness and refractive index of the porous dielectric layer 21 in a state where a thickness of the metal layer 24 is fixed at 20 nm. Referring first to FIG. 7A, it can be noted that the reflectivity-sensitivity is increased as it goes toward the center of the graph. That is, while a thickness of the porous dielectric layer 21 is varied from 800 nm to 1400 nm, the reflectivity-sensitivity is gradually increased and then gradually decreased. Likewise, while a refractive index is varied from 1.31 to 1.36, the reflectivity-sensitivity is gradually increased and then gradually decreased. FIG. 7B shows an enlarge graph of a thickness section from 1050 nm to 1350 nm of the porous dielectric layer 21 and a refractive index section from 1.333 to 1.355 of the porous dielectric layer 21. As shown in FIG. 7B, when a thickness and refractive index of the porous dielectric layer 21 are respectively 1300 nm and 1.35, the reflectivity-sensitivity becomes maximized.

Figure 8A:
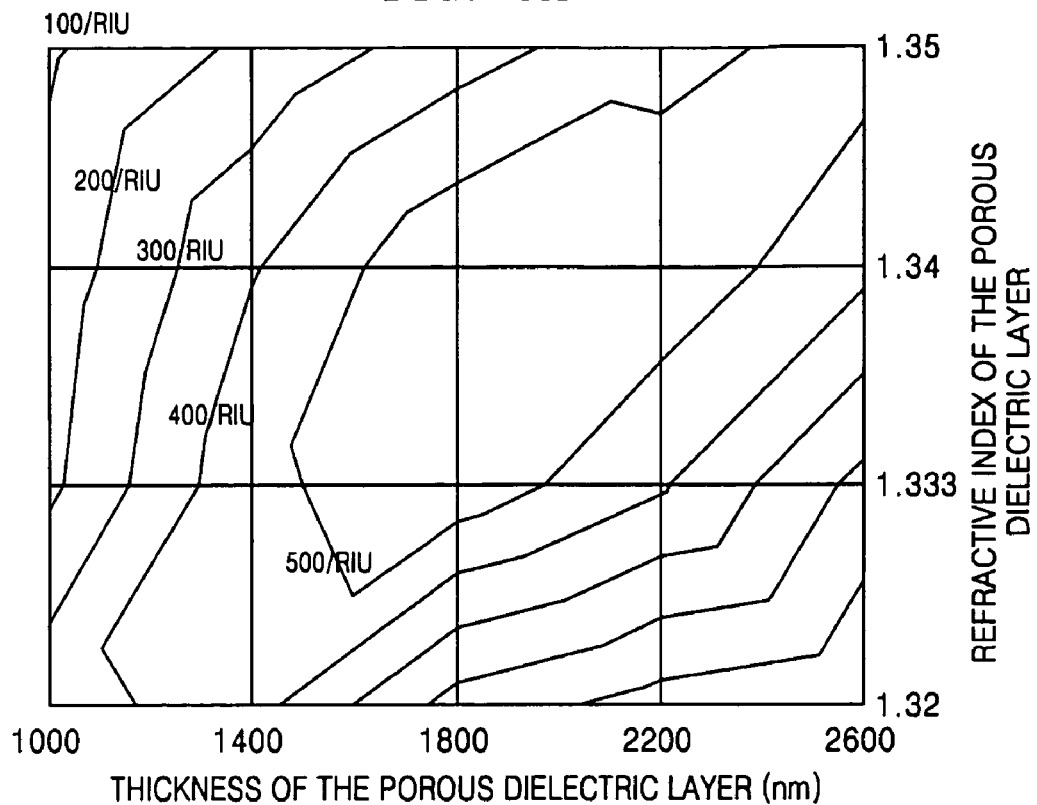
Figure 8B:
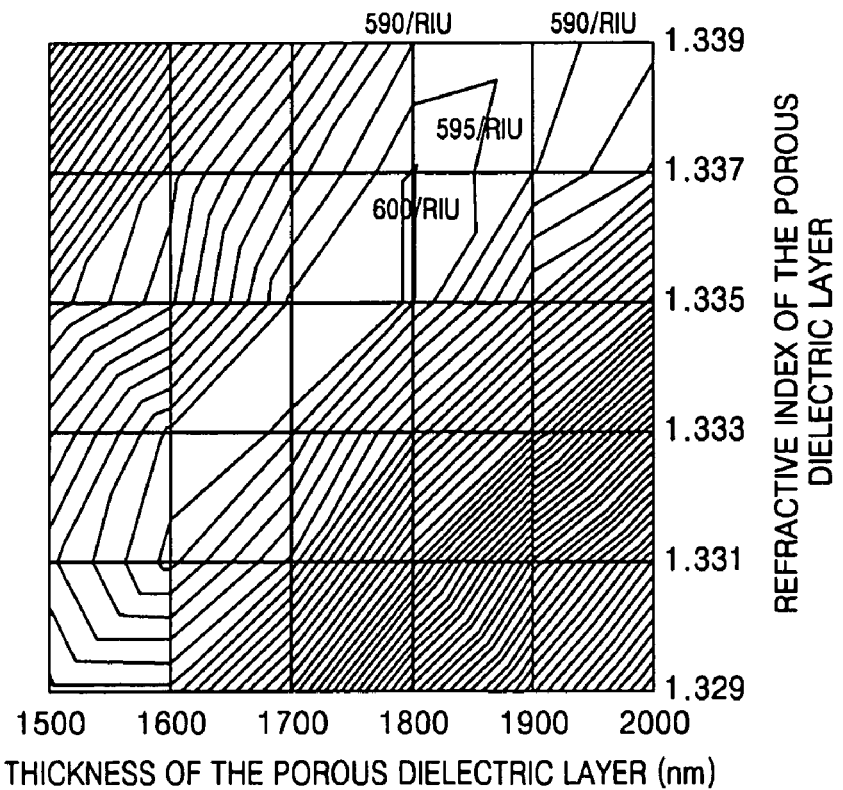

FIGS. 8A and 8B show a simulation result of the variation of the reflectivity-sensitivity according to the variations of a thickness and refractive index of the porous dielectric layer 21 in a state where a thickness of the metal layer 24 is fixed at 12 nm. Referring to FIG. 8A, it can be noted that the reflectivity-sensitivity is increased as it goes toward the center of the graph. FIG. 8B shows an enlarge graph of a thickness section from 1500 nm to 2000 nm of the porous dielectric layer 21 and a refractive index section from 1.329 to 1.339 of the porous dielectric layer 21. As shown in FIG. 8B, when a thickness and refractive index of the porous dielectric layer 21 are respectively about 1700 nm and 1.333, the reflectivity-sensitivity becomes maximized. At this point, the maximum value of the reflectivity-sensitivity is about 600/RIU greater than 178/RIU that is a maximum value obtained when the thickness of the thin metal layer 24 is 20 nm.

Through the above-described simulation results, a variety of optimized parameters such as the refractive index and thickness of the porous dielectric layer 21 can be calculated in advance according to the samples. The long-range surface plasmon resonance device can be fabricated according to the optimized refractive index and thickness.

FIG. 9 shows a flowchart illustrating a method of fabricating a long-range surface plasmon resonance device. Referring to FIG. 9, a variety of optimized parameters of the long-range surface plasmon resonance are first determined according to the samples through by a simulation. For example, a variety of optimized parameters such as a thickness of the thin metal layer 24, a thickness of the porous dielectric layer 21, a refractive index of the porous dielectric layer 21, a material of the thin metal layer 24, materials of the transparent substrate 20 and the prism 25, a wavelength of the light source, and the like are determined. Then, as illustrated with reference to FIGS. 4A and 4B, the porogen 22 is mixed with and dispersed in the dielectric material at a predetermined ratio and deposited on the transparent substrate 20 to provide a desired refractive index. Then, a heat treatment is performed to crystallize the dielectric material and remove the porogen 22 from the dielectric material, thereby forming the porous dielectric layer 21. The thin metal layer 24 having a predetermined thickness calculated in advance is deposited on the porous dielectric layer 21 and the prism is attached on the transparent substrate 20, thereby providing an optimized long-range surface plasmon resonance device.

According to the present invention, it is possible to properly adjust the refractive index of the buffer layer. Therefore, an optimized long-range surface plasmon resonance device can be fabricated. As a result, it is possible to obtain high resolution as well as high sensitivity. Furthermore, it is possible to detect even a micro-variation of the refractive index of the liquid sample. Therefore, it is possible to detect even a very small amount of material contained in the liquid sample.

In the prior art, since there are few materials that can be used for the buffer layer of the long-range surface plasmon resonance device, only liquid samples using water as a solvent have been generally used as analytes. However, according to the present invention, since it is possible to fabricate an optimized long-range surface plasmon resonance device according to the samples, the solvent of the samples is not limited to the water. That is, it becomes possible to fabricate a surface plasmon resonance device that is capable of detecting samples using other types of solvents in addition to water.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A surface plasmon resonance device comprising:
   a transparent substrate;
   a porous dielectric layer formed on a top surface of the transparent substrate;
   a thin metal layer formed on the porous dielectric layer; and
   a prism attached on a bottom surface of the transparent layer.

2. The surface plasmon resonance device of claim 1, wherein the porous dielectric layer has an adjusted refractive index obtained by adjusting a density of porosities formed in the porous dielectric layer.

3. The surface plasmon resonance device of claim 2, wherein the porous dielectric layer has refractive index of 1.31 to 1.46.

4. The surface plasmon resonance device of claim 1, wherein the porous dielectric layer is formed by vaporizing porogen through a heat treatment after the porogen is dispersed in a dielectric material.

5. The surface plasmon resonance device of claim 4, wherein the dielectric material contains at least one of silane and siloxane polymer.

6. The surface plasmon resonance device of claim 4, wherein the porogen contains cyclodextrin.

7. The surface plasmon resonance device of claim 1, wherein a size of each porosity formed in the porous dielectric layer is less than 10 nm.

8. The surface plasmon resonance device of claim 1, wherein the thin metal layer contains Au.

9. The surface plasmon resonance device of claim 1, wherein a thickness of the thin metal layer is less than 20 nm.

10. The surface plasmon resonance device of claim 1, wherein the prism has a refractive index identical to that of the transparent substrate.

11. A method of fabricating a surface plasmon resonance device, the method comprising:
    mixing and dispersing porogen with and in a dielectric material;
    depositing the dielectric material mixed with the porogen on a transparent substrate to a predetermined thickness;
    performing a heat treatment to form a porous dielectric layer by crystallizing the dielectric material and vaporizing the porogen dispersed in the dielectric material;
    depositing a thin metal layer on the porous dielectric layer; and
    attaching a prism on a bottom surface of the transparent substrate.

12. The method of claim 11, wherein a mixture ratio of the dielectric material and the porogen is determined according to parameters of the surface plasmon resonance device that is optimized according to a sample that is to be measured.

13. The method of claim 12, wherein the parameters comprise a refractive index of the porous dielectric layer, a thickness of the porous dielectric layer, a refractive index of the transparent substrate, a thickness of the thin metal layer, and a wavelength of a light source.

14. The method of claim 12, wherein a mixture ratio of the dielectric material and the porogen is determined according to a refractive index of the porous dielectric layer.

15. The method of claim 11, wherein a size of each porosity formed in the porous dielectric layer is less than 10 nm.

16. The method of claim 11, wherein the dielectric material contains at least one of silane and siloxane polymer.

17. The method of claim 11, wherein the porogen contains cyclodextrin.

18. The method of claim 11, wherein the heat treatment is performed at 450° C.

19. The method of claim 11, wherein the thin metal layer contains Au.

20. The method of claim 11, wherein a thickness of the thin metal layer is less than 20 nm.

21. The method of claim 11, wherein the prism has a refractive index identical to that of the transparent substrate.

* * * * *